United States Patent
Whittle et al.

(10) Patent No.: US 7,341,746 B2
(45) Date of Patent: *Mar. 11, 2008

(54) CHINESE HERBS EXTRACT

(75) Inventors: Brian Anthony Whittle, Hornsea (GB); Jonathan Brostoff, London (GB); Yvette Latchman, Woodford Green (GB)

(73) Assignee: Phytotech Limited, Godmanchester (GB)

( * ) Notice: Subject to any disclaimer, the term of this patent is extended or adjusted under 35 U.S.C. 154(b) by 316 days.

This patent is subject to a terminal disclaimer.

(21) Appl. No.: 10/716,506

(22) Filed: Nov. 20, 2003

(65) Prior Publication Data

US 2004/0101581 A1    May 27, 2004

Related U.S. Application Data

(63) Continuation of application No. 10/074,039, filed on Feb. 14, 2002, now Pat. No. 6,676,975, which is a continuation of application No. 08/750,848, filed as application No. PCT/GB95/01471 on Jun. 23, 1995, now Pat. No. 6,399,112.

(30) Foreign Application Priority Data

Jun. 24, 1994    (GB) ................................ 9412755.2

(51) Int. Cl.
     *A61K 36/00*    (2006.01)
(52) U.S. Cl. ...................... 424/725; 424/773; 424/777; 514/861; 514/863; 514/885; 514/886; 514/887
(58) Field of Classification Search ...................... None
     See application file for complete search history.

(56) References Cited

U.S. PATENT DOCUMENTS

| | | | | |
|---|---|---|---|---|
| 3,131,175 | A * | 4/1964 | Kalkstein .................... | 536/18.5 |
| 4,940,725 | A | 7/1990 | Keplinger et al. .......... | 514/411 |
| 5,466,452 | A | 11/1995 | Whittle | |
| 6,399,112 | B1 | 6/2002 | Whittle | |
| 2004/0101581 | A1 * | 5/2004 | Whittle et al. .............. | 424/757 |

FOREIGN PATENT DOCUMENTS

| | | |
|---|---|---|
| GB | 2254783 | 10/1992 |
| GB | A-2 254 783 | 10/1992 |
| JP | 56138120 | 10/1981 |
| JP | A-60181022 | 9/1985 |
| WO | WO-87/06833 | 11/1987 |
| WO | WO 92/15314 | 9/1992 |

OTHER PUBLICATIONS

Castleman, M. The Healing Herbs—The Untimate Guide to the Curative Power of Nature's Medicines. 1991. Rodale Press, Emmaus, PA, pp. 236-240.*
Galloway et al., The Lancet, 337:556, 1991.
Holgate et al., Allergy Gower Medical Publishing, London, UK, Chapter 7, p. 7.1-7.10, 1993.
Harper et al., *The Lancet*, 335(8692), Mar. 31, 1990, p. 795.
Paul-Eugene et al. (1993), *Molecular Immunology*, 30, No. 2, pp. 157-164.
Kaufman Paterson et al. (Feb. 15, 1994), *J. of Immunol.*, 152, pp. 2139-2147.
Mowrey, The Scientific Validation of Herbal Medicine, Keats Publishing, Inc., New Canaan, CT, p. 25-30, 1986.
Lawless, The Illustrated Encyclopedia of Essential Oils, The Complete Guide to the Use of Oils in Aromatherapy and Herbalism, Element Boks, Inc., Rockport, MA, p. 48, 1996.
Gessl et al. (1993), *Immunology*, 78, pp. 476-481.
Katira et al. (1993), *Clin. Exp. Immunol.*, 92, pp. 347-352.
Williams et al. (1992), *J. of Immunol.*, 149, pp. 2823-2829.
Willheim et al. (1991), *J. of Immunol.*, 147, pp. 1837-1842.
Fargeas et al. (1990), *J. of Immunol.*, 145, pp. 4053-4058.
Te Velde et al.(1990), *J. of Immunol.*, 144, pp. 3052-3059.
Galizzi et al. (1988), *J. of Immunol.*, 141, 1982-1988.
Vercelli et al. (1988), *J. Exp. Med.*, 167, pp. 1406-1416.
Bieber et al. (1989), *J. Exp. Med.*, 170, pp. 309-314.
Sheehan et al. (1992), *Brit. J. of Dermatol.*, 126, pp. 179-184.
Sheehan et al. (Jul. 4, 1992), *The Lancet*, 340, pp. 13-17.
Takigawa et al. (1994), *Clin. Exp. Immunol.*, 84, pp. 275-282.
Galloway et al. (1991), *The Lancet*, 337, p. 566.
M. Harada, "The Pharmacology of Peony", Gendaitoyouigaku, 1985, vol. 6, No. 1, pp. 45-50.
T. Okuda, "Encyclopedia of Natural Medicinal Substances", Tokyohirokawa, 1986 p. 127.

* cited by examiner

*Primary Examiner*—Christopher R. Tate
(74) *Attorney, Agent, or Firm*—Bacon & Thomas PLLC

(57) ABSTRACT

This application relates to a material which is suitable for the treatment of atopic disease, non-atopic eczema or psoriasis. The material can be extracted from a freeze-dried decoction of a mixture comprising the following Chinese herbs: *Radix Ledebouriella, Fructus Tribuli, Herba Potentilla chinensis, Caulis Clematis armandii, Radix Rehmannia, Radix Glycyrrhiza, Radix Paeonia rubra, Cortex Dictamni radicis, Herba Lopatheri, Spica Schizonepetae*. The material comprises one or more of those components present in the freeze-dried decoction which run with Rf values in the ranges 0.00 to 0.100, 0.167 to 0.300, 0.400 to 0.533, 0.700 to 0.833 or 0.900 to 0.967 if the freeze-dried decoction is diluted in aqueous solution and subjected to chromatography on a Whatman 2 cms×55 cms×3 mm cellulose strip for 10 hours using a solvent mixture of butanol, ethanol and water in the proportions 4:1:1.

10 Claims, 3 Drawing Sheets

CHINESE HERBS EXTRACT

Figure 1A:
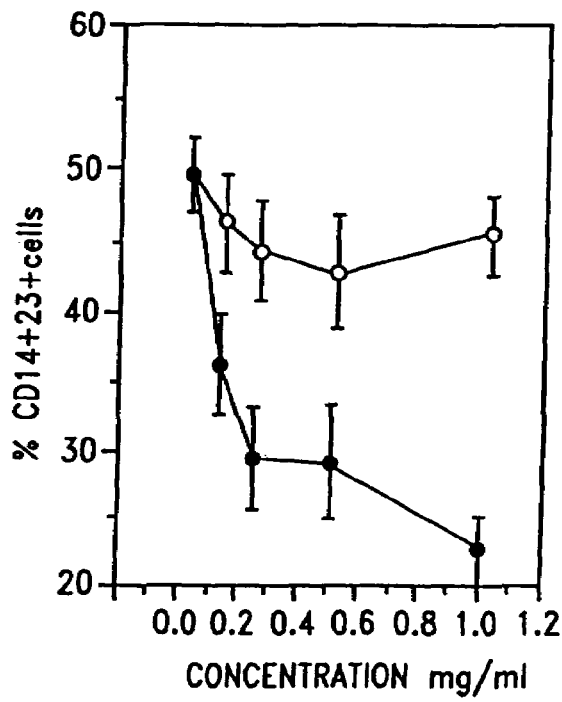

This application is a continuation of nonprovisional application Ser. No. 10/074,039 filed on Feb. 14, 2002, now U.S. Pat. No. 6,676,975 which is a continuation application of nonprovisional application Ser. No. 08/750,848 filed on Dec. 24, 1996, and which has now issued as U.S. Pat. No. 6,399,112 on Jun. 4, 2002, which is the U.S. national phase of International Application No. PCT/GB95/01471 filed on Jun. 23, 1995.

The invention relates to materials derived from traditional Chinese herbs and to pharmaceutical compositions containing them which are useful in the treatment of atopic disease, in particular atopic eczema, and in treatment of other skin disorders such as non-atopic eczema and psoriasis.

It is to be understood that by the term Chinese herb is meant any herb which is used by traditional medicine practitioners, usually, but not exclusively, Chinese.

Practitioners of traditional Chinese medicine treat diseases using a system of anatomy and diagnosis totally different from that used in the west. The remedies prescribed are usually a plurality of Chinese herbs which are prepared for administration by the traditional method of decoction i.e. boiling the herbs in water. The herbs are removed and the water maintained for oral, parenteral or topical administration to the patient as appropriate.

Prescriptions for use in this kind of therapy may call for the use of ten or more herbs in combination and traditional Chinese medicine teaches that all of the herbs are necessary to achieve a balanced prescription. A prescription is seen as a balanced whole containing the hierarchy of herbs to which are attributed different functions in treating different manifestations and symptoms of disease.

The identification of herbs which have acceptable clinical activity for any particular human disease while, at the same time having low toxicity, has been made by observation and trial and error over very many years. In some cases prescriptions of traditional Chinese herbs can effectively treat diseases which are not well served by Western monotherapy.

Diseases which appear to respond to the use of a plurality of Chinese herbs are those where there is obscure and complex causality. A particular example is atopic eczema, in which there is chronic inflammation of the skin which is initiated and maintained by a number of different mediators, only some of which are known. Some are related to antigen-antibody reactions. Many others are suspected but not yet defined. Single therapeutic agents like non-steroidal anti-inflammatory drugs which interact with specific inflammatory mediators such as prostaglandins are ineffective in severe atopic eczema. On the other hand corticosteroids have multiple pharmacodynamic actions and are effective in eczema. It appears therefore that the treatment of severe atopic eczema requires a simultaneous attack on a number of pathological lesions, probably related to the immune process in cells and body fluids. While corticosteroids and some immune suppressants have the required broad spectrum of activity for such an attack, their use is limited because of their toxicity. Traditional Chinese herbal remedies known for the treatment of eczema would seem to possess the necessary activity of corticosteroids and immune suppressants but not their toxicity.

A prescription of the Chinese herbs with one selected from each of the following herbs and their Pin yin equivalents or designated by their Materia Medica names:—*Radix Ledebouriella, Fructus Tribuli, Herba Potentilla chinensis, Caulis Clematis armandii, Radix Rehmannia, Radix Glycyrrhiza, Radix Paeonia rubra, Cortex Dictamni radicis, Herba Lopatheri* and *Spika Schizonepetae* has been used to effectively treat atopic eczema and psoriasis. The clinical efficacy of such a prescription in children with atopic eczema is described by Sheehan et al in British Journal of Dermatology (1992) 126 pp 179-184 and in adults, again by Sheehan et al, in The Lancet (1992) July 4th pp 13-17. A particular method for preparing an extract of those same 10 herbs for use in treating atopic eczema and other inflammatory diseases of the skin is described in GB-A-2254783.

While a decoction of the above-described 10 herbs is known to be effective, the use of a complex prescription containing a plurality of herbs is expensive and it is therefore desirable to simplify the prescription if this can be done without compromising activity and/or safety. It would also be preferable to limit any prescription to herbs which might be grown in the UK or Europe rather than relying on import from China. Thus many attempts have been made to identify the active principle or principles in prescriptions of traditional Chinese medicines. In the case of eczema however this has proved difficult because hitherto there has been no validated animal or in vitro model for the disease which could be used to identify clinical activity in fractions or pure substances prepared from the crude herbs.

Now however an in vitro assay has been developed which appears to be predictive of clinical efficacy in atopic eczema and other atopic diseases and this has allowed the present inventors to detect active components in freeze-dried decoctions (hereinafter referred to as PSE222) of the 10 herbs listed above.

Although traditional Chinese wisdom dictates that a plurality of herbs is required, the use of this in vitro method and confirmation by in vivo clinical experiments has shown that the desired clinical effect can be reproduced by a subset of the 10 herbs and by individual components within them. Furthermore, the method has also permitted identification of components in PSE222 which may initiate worsening of the atopic condition and which it is desirable to remove from any extract for pharmaceutical use.

The in vitro test for efficacy is based on the observation that in atopic disease and in particular atopic eczema, skin cells and monocytes from human peripheral blood express a cell surface marker antigen CD23 and that the expression of CD23 is inhibited or reduced on successful treatment of the eczema. (see Takigawa et al, Clin. Exp. Immunol. (1991) 84 pp 275-282). CD23 expression can also be induced in vitro in human monocytes by exposure to the cytokine interleukin 4 (IL4) and in parallel with the in vivo situation described by Takigawa above the induction is inhibited by compounds known to be useful in atopic disease. These observations therefore provide the basis for a simple in vitro assay in which monocytes prepared from human peripheral blood are brought into contact simultaneously with IL4 and the active agent to be tested. The amount of CD23 expression is measured using labelled monoclonal antibodies to CD23 and any effect expressed as a percentage inhibition of CD23 expression compared to a control in which saline or a placebo preparation of herbs replaces the test material. That significant inhibition of CD23 expression in this in vitro test is predictive of clinical efficacy is demonstrated by the fact that the extract PSE222, prepared from the 10 herbs listed above which have been successfully used clinically for atopic eczema, shows an inhibition of CD23 expression in the assay of 50 to 60%.

Using the above assay the present inventors have identified components in PSE222 suitable for clinical use in atopic disease generally and also in the treatment of particular skin diseases such as non-atopic eczema and psoriasis.

Thus in accordance with a first aspect of the invention there is provided a material suitable for the treatment of atopic disease, non-atopic eczema or psoriasis which can be extracted from a freeze-dried decoction of a mixture comprising the following Chinese herbs:

Radix Ledebouriella
Fructus Tribuli
Herba Potentilla chinensis
Caulis Clematis armandii
Radix Rehmannia
Radix Glycyrrhiza
Radix Paeonia rubra
Cortex Dictamni radicis
Herba Lopatheri
Spika Schizonepetae said material comprising one or more of those components present in the freeze-dried decoction which run with Rf values in the ranges 0.00 to 0.100, 0.167 to 0.300, 0.400 to 0.533, 0.700 to 0.833 or 0.900 to 0.967 if said freeze-dried decoction is diluted in aqueous solution and subjected to chromatography on a Whatman 2 cms×55 cms×3 mm cellulose strip for 10 hours using a solvent mixture of butanol, ethanol and water in the proportions 4:1:1.

Preferably said material comprises one or more of those components present in the freeze-dried decoction which run with Rf values in the range 0.00 to 0.100.

When the cellulose strip is subjected to a water extraction after the solvent front has run some 30 cm or so those components extracted with the water having Rf values roughly in the ranges given above cause significant reduction of CD23 antigen on human monocytes treated in vitro with IL4. If the cellulose strip is subsequently extracted with methanol, the methanol extracts for those components having an Rf values roughly in the ranges 0.700 to 0.833 or 0.900 to 0.967 also cause significant reduction in CD23 expression in vitro.

Furthermore, and surprisingly, following a water extraction and subsequent methanol extraction of the cellulose strip, those methanol extracts of components running with Rf values in the ranges of 0.067 to 0.333 and 0.533 to 0.700 when tested in the CD23 assay, enhance or increase the expression of the CD23 antigen compared to controls. The presence of the "enhancer" activity in any preparation for the treatment of atopic or non-atopic eczema or other atopic disease is clearly undesirable and enhanced clinical activity is thus predicted on its removal. A significant amount of the "enhancer" activity may be removed by extraction of PSE222 or other preparation of the 10 herbs listed above with a non-polar solvent such as hexane.

Therefore in accordance with a second aspect of the invention there is provided a material for the treatment of atopic eczema, non-atopic eczema or psoriasis which comprises a decoction or extract of a mixture including the ten Chinese herbs listed above which has had those components, extractable with hexane or other non-polar solvent, removed. A decoction or extract so treated demonstrates significant inhibition of CD23 expression on human monocytes in the above described in vitro assay which is indicative of its potential clinical efficacy.

Decoctions of the individual herbs from the above list of ten have been tested for their ability to inhibit CD23 expression in vitro and this has lead to the identification of a subset of herbs predicted to have good clinical efficacy.

In accordance with a third aspect of the invention there is provided a material for the treatment of atopic disease, non-atopic eczema or psoriasis which comprises a decoction or extract of one or more of the following sets of Chinese herbs:

(a) Radix Paeonia rubra
Radix Glycyrrhiza
Radix Rehmannia (b) Cortex Dictamni
Radix Paeonia rubra
Radix Glycyrrhiza
Radix Rehmannia
Radix Ledebouriella
Fructus Tribuli or (c) Radix Paeonia rubra
Radix Glycyrrhiza
Spika Schizonepetae in the substantial absence of any other Chinese herbs. Preferably such a decoction or extract is treated so that those components extractable with hexane or other non-polar solvent have been removed. The sets of herbs specified under (a) and (c) above have the advantage that all the herbs used can be grown in Europe.

In accordance with a fourth aspect of the invention there is provided a material for treatment of atopic disease, non-atopic eczema and psoriasis which comprises a decoction or extract from one or more of the herbs Cortex Dictamni, Radix Paeonia rubra, Radix Rehmannia, Radix Glycyrrhiza or Spika Schizonepetae in the substantial absence of any other Chinese herbs. Again, preferably such extracts or decoctions are subject to extraction with a non-polar solvent such as hexane.

Production of the active components of PSE222 on a commercial scale may be achieved by contacting a freeze-dried decoction with fibrous cellulose, of which suitable grades are available commercially, followed by mixing with a suitable solvent such as the butanol/ethanol/water mix as described above or butanol/IMS/water mix in the proportions 4:1:1 to remove bulk and inactive materials. Centrifugation of the mix then yields a precipitate which can be re-extracted with the above solvent mix several times before drying and mixing with water to extract the active components for formulation as pharmaceutical preparations.

The materials of the first, second, third and fourth aspects of the invention, whether or not produced by the above-described commercial process, are preferably prepared as pharmaceutical compositions by mixing with any suitable pharmaceutical carrier or diluent, of which a great many are known in the art. Compositions suitable for treatment of atopic disease generally, and in particular atopic eczema or for non-atopic eczema or psoriasis may be formulated for oral, topical or parenteral administration. Oral formulations may be prepared in unit dosage forms as for example tablets, powders or granules or may be a liquid preparation for drinking.

It will be appreciated that the in vitro assay described above may be used as an indicator of any compound or preparation which is likely to be clinically active against atopic eczema and dermatitis irrespective of geographical or botanical origin.

Thus in accordance with a fifth aspect of the invention there is provided a method for indicating the clinical activity of a compound or preparation against atopic eczema or dermatitis which comprises the steps of:

(a) incubating peripheral blood monocytes in vitro simultaneously or sequentially with interleukin 4 (IL4) and the compound or preparation whose activity is to be tested, (b) measuring the expression of the cell surface marker CD23 on said monocytes and (c) using the measurements obtained in step (b) as an indication of potential clinical efficacy of the compound or preparation against atopic eczema or dermatitis by comparing the level of IL4 induced CD23 expression of the monocytes in the presence or absence of said compound or preparation.

An inhibition of CD23 expression of greater than 25% is statistically significant and indicates a compound or preparation which may be clinically useful.

Figure 1B:
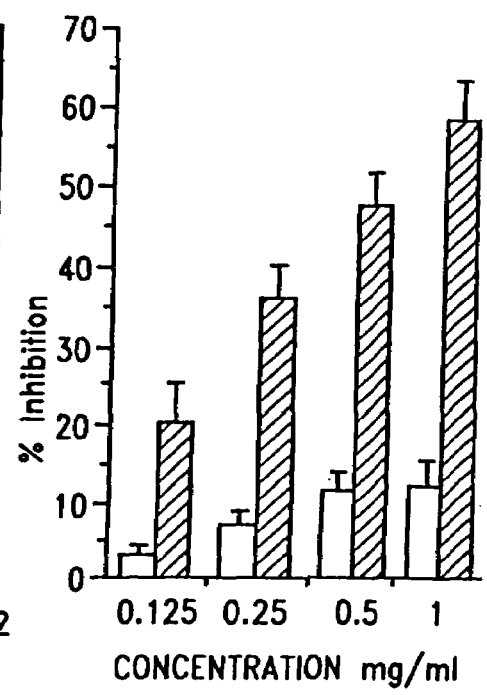
Figure 1C:
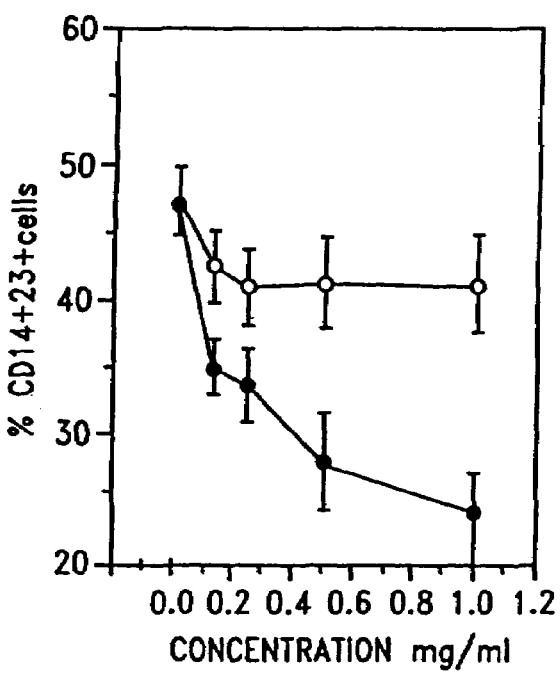
Figure 1D:
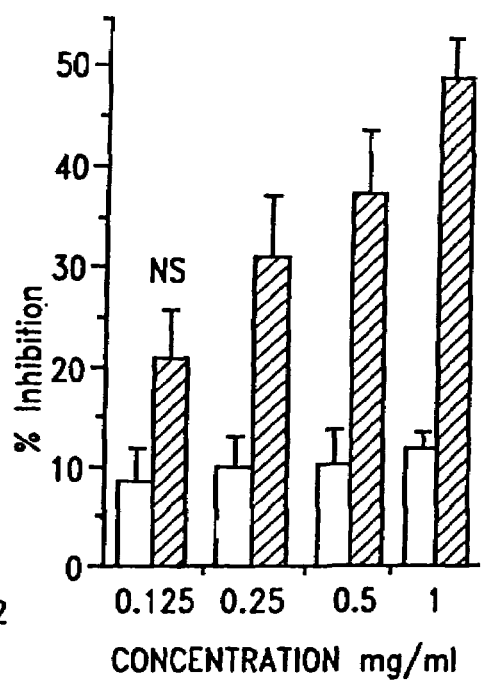
Figure 2:
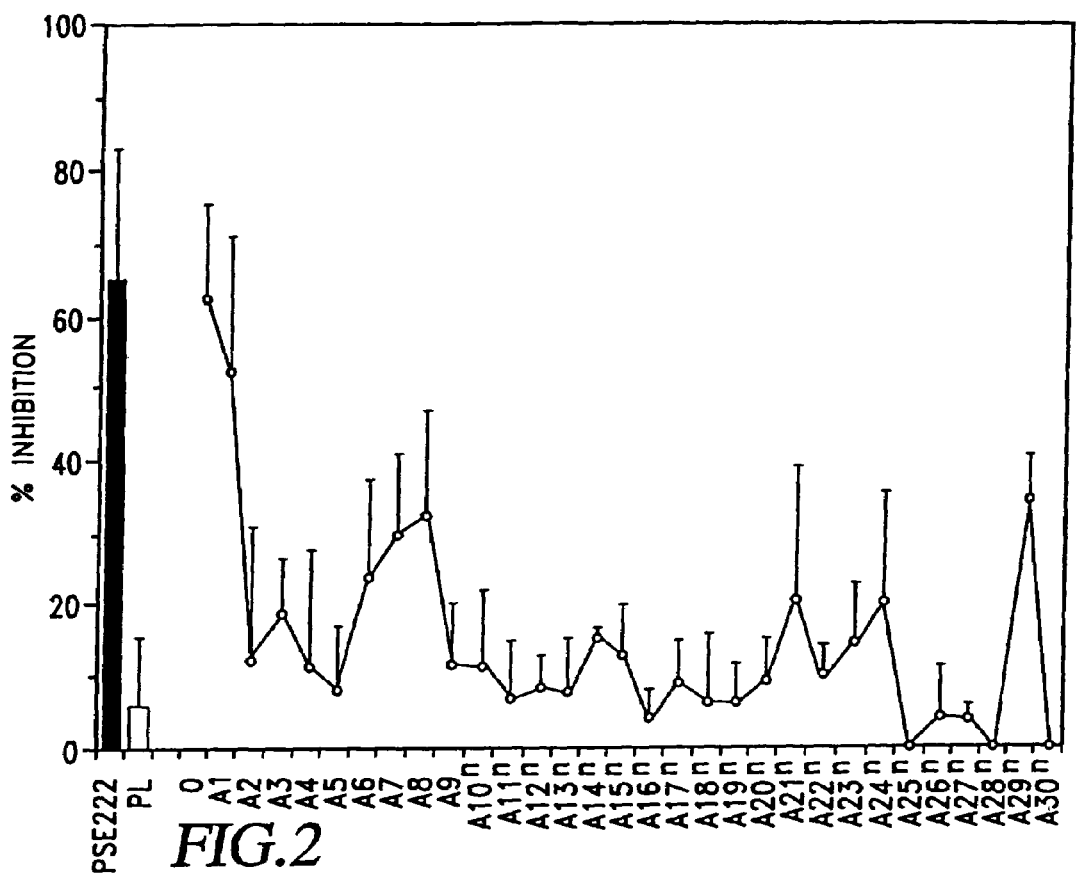
Figure 3:
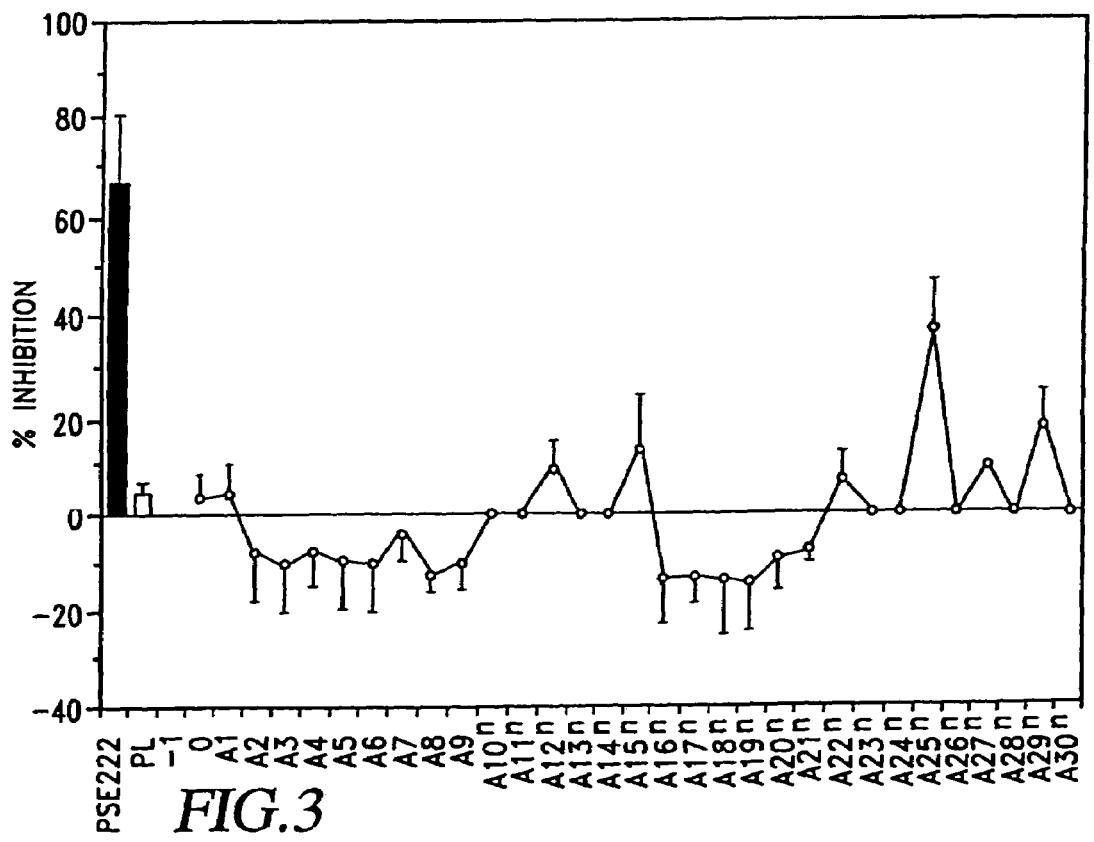
Figure 4:
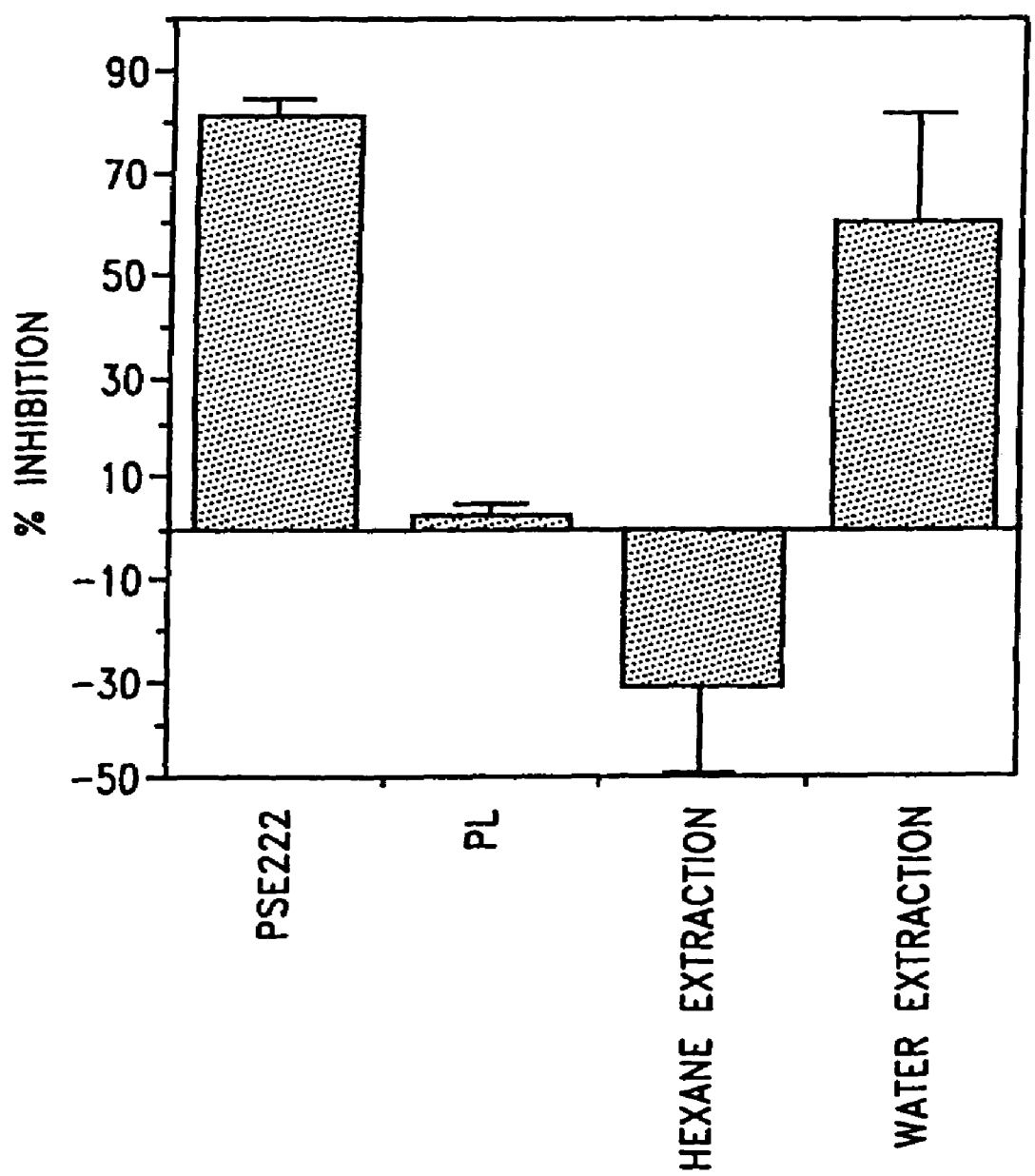

The invention will now be described with reference to the following Examples and drawings in which:

FIG. 1a is a plot of the percentage of CD14+23+monocytes against concentration of test material used in the assay for PSE222 (*) and for a mixture of placebo herbs (○) using monocytes from patients with atopic eczema, FIG. 1b shows the same data as FIG. 1a represented as a histogram with percentage inhibition of CD23 expression on the y axis. Cross-hatched blocks represent PSE222 data and open blocks the placebo control, FIG. 1c is a plot as in FIG. 1a showing the effect of PSE222 on CD23 expression in monocytes from normal individuals, FIG. 1d shows the same data of FIG. 1c in histogram form as in FIG. 1b, FIG. 2 shows percentage inhibition of CD23 expression in human monocytes in vitro for each of 30 fractions extracted from a cellulose chromatography strip with water, FIG. 3 shows percentage inhibition of CD23 expression in human monocytes in vitro for each of 30 fractions extracted from a cellulose chromatograph strip with methanol, and FIG. 4 shows the effect on CD23 expression in vitro of hexane extraction of PSE222.

EXAMPLE 1

A total weight of 38.8 g of the following herbs was simmered for one and a half hours in 300 ml of water:

Radix Ledebouriella
Fructus Tribuli
Herba Potentilla chinensis
Caulis Clematis armandii
Radix Rehmannia
Radix Glycyrrhiza
Radix Paeonia rubra
Cortex Dictamni radicis
Herba Lopatheri
Spika Schizonepetae The herbs were removed, the decoction concentrated to a final volume of 50 ml by boiling and then freeze-dried. In the freeze-dried extract PSE222, one gram of dried extract contained the water extractive from approximately 5 grams of herb.

A decoction of "placebo" herbs having no known efficacy against atopic eczema was prepared in the same way as described above.

The activity of PSE222 and the placebo decoction was examined in the CD23 inhibition assay which was carried out as set out below.

Blood was collected from a volunteer into heparin and separated on a Ficoll gradient to isolate the peripheral blood mononuclear cells (monocytes). The monocytes were then cultured overnight in RPMI with IL4 and with or without PSE222 or placebo preparation. Thereafter monocytes were washed and double-stained using fluorescein-labelled monoclonal antibodies against monocyte antigens CD14 and CD23. CD14 is a useful marker which when present confirms the presence of monocytes. The level of fluorescein was measured using FACScan analysis and provided an indication of the level of CD23 expression by the monocytes.

The results are shown in FIGS. 1a to d. As is apparent from FIGS. 1a and 1c, PSE222 inhibited IL4 induced CD23 expression in both monocytes from patients with atopic eczema (1a) and normal individuals (1c). Further, the effect was dose-dependent and there was a statistically significant difference ($P<0.001$) between PSE222 and placebo treatment. FIGS. 1b and 1d confirm that a statistically significant inhibition of CD23 of about 25 to 30% occurred at PSE222 concentrations as low as 0.125 mg/ml for monocytes from patients with atopic eczema. In the case of monocytes from normal patients a statistically significant inhibition did not occur until the PSE222 concentration was about 0.25 mg/ml.

On the basis of the above results a percentage inhibition of CD23 expression of between 25 and 30% is used as the criterion for assessing and predicting clinical activity for alternative test preparations. In clinical studies carried out in patients with severe atopic eczema it has been shown that the PSE222 formulation, but not the placebo preparation, produces a 60-80% reduction in the severity of the eczema in two-thirds to three-quarters of patients. This result is statistically significant ($P=0.01$).

EXAMPLE 2

A decoction of the individual herbs listed in Table 1 below was prepared by the method described in Example 1 and a dried extract prepared for each herb. 1 mg quantities of each extract (equivalent to 5 mg of raw herb and diluted to a concentration equivalent to that in the PSE222 preparation) were tested for in vitro inhibition of CD23 expression, also as described in Example 1. The results are shown in Table 1 below, each value given representing the mean of 5 experiments.

TABLE I

| Conc$^n$ mg/ml | Herb/Constituent | % Inhibition of CD23/CD14 |
|---|---|---|
|  | IL4 (control, baseline) | 0 |
| 1 | (a) IL4 + PSE222 | 55.8 |
| 1 | (b) IL4 + Placebo herbs | 3.4 |
| 0.12 | (c) Cortex Dictamni | 43.6 |
| 0.11 | (d) Radix Paeonia rubra | 48.0 |
| 0.05 | (e) Radix Glycyrrhiza | 47.0 |
| 0.30 | (f) Radix Rehmannia | 20.5 |
| 0.07 | (g) Radix Ledebouriella | 3.0 |
| 0.06 | (h) Fructus Tribuli | 4.6 |
| 0.08 | (i) Potentilla chinensis | 6.6 |
| 0.03 | (j) Clematis armandii | 16.0 |
| 0.04 | (k) Spika Schizonepetae | 43.6 |
| 0.15 | (l) Herba Lopatheri | 16.6 |

The clinical efficacy of certain subsets of the herbs (c) to (l) listed in Table I above was tested and the results are shown in Table II.

TABLE II

| Herb Sunsets | Clinical Activity | Statistical Significance |
|---|---|---|
| a(PSE222) | ++++ | P < 0.01 |
| e | ± | |
| d,e,f | +++ | |
| c,d,e,f,g,h | ++ | P < 0.05 |
| d,e,k | +++ | P < 0.05 |

Key
++++ >70% reduction in total eczema score
+++ 60-70% reduction in total eczema score
++ <60% reduction in total eczema score
± No consistent improvement.

For herb (e), Radix Glycyrrhiza, a component is known to have some clinical activity when applied locally but it cannot be given alone in high doses by mouth because of steroid-like adverse effects, e.g. it is electrolyte-disturbing.

The results given in Table I and Table II confirm that CD23 inhibition in vitro is largely predictive of clinical efficacy in atopic eczema.

EXAMPLE 3

75 mg of PSE222 was added to RPMI 1640 incubation medium and made up to a volume of 10 mls, incubated at 37° C. with occasional agitation and centrifuged to remove fines and other debris. 500 µl of a 1:10 dilution of the resulting solution was loaded onto a Whatman 3 mm×2 cms×55 cms cellulose strip. The loaded end of the strip was placed in a mixture of butanol/ethanol/water in the proportions 4:1:1 and the solvent allowed to move by capillarity for 10 hours after which time the solvent front had moved about 30 cms. The strip was allowed to dry overnight and then cut into 2×1 cm pieces. These pieces were each eluted with 20 µl/cm$^2$ of water and the eluate evaporated to dryness and resuspended in 500 µl RPMI 1640 incubation medium for testing in the CD23 assay. In all 29 fractions were prepared and FIG. 2 shows the CD23 inhibitory activity of each as well as entire PSE222 and placebo herbs. Strip 30, corresponding to the solvent front, was used as the internal control in the CD23 expression assay.

As can be seen from FIG. 2, peaks of inhibitory activity were found particularly in fraction A0 (origin) and then in fractions 1, 3, 6, 7, 8, 14, 15, 21, 25 and 29, the fraction numbers corresponding to centimetres from the origin. These fractions correspond to Rf values 0.00, 0.033, 0.100, 0.200, 0.233, 0.267, 0.467, 0.500, 0.900, 0.833 and 0.967 respectively.

After eluting the 2×1 cm pieces with water and testing the eluate as described above, the pieces were dried and then eluted with 20 µl/cm$^2$ of methanol. The eluate was again evaporated to dryness and resuspended in 500 µl of RPMI 1640 incubation medium for testing in the CD23 assay. The level of CD23 inhibiting activity in each fraction following methanol extraction is shown in FIG. 3. There were distinct peaks of inhibitory activity found in 25, 27 and 29 corresponding to Rf values of 0.833, 0.900 and 0.967.

The components of the active fractions shown in FIGS. 2 and 3 are suitable for use in pharmaceutical compositions for treating atopic eczema and other atopic diseases as well as psoriasis.

Interestingly, following water and then methanol extraction as described above fractions 2 to 9 and 16 to 21 corresponding to Rf ranges 0.067 to 0.300 and 0.533 to 0.700 respectively, when tested in the CD23 assay, enhanced CD23 expression significantly rather than inhibiting it.

EXAMPLE 4

A solution of PSE222 prepared as described in Example 1 was extracted with hexane. The hexane fraction was evaporated to dryness, resuspended as described above and tested in the CD23 assay. The hexane extract significantly increased CD23 expression above control. However a subsequent water extract of the hexane extracted PSE222 showed the expected inhibition of CD23 expression. The results are shown in FIG. 4.

This example confirms the usefulness of extracting any of the 10 herbs of PSE222 with a non-polar solvent to remove undesirable components from any potential pharmaceutical composition.

EXAMPLE 5

1 g of finely powdered freeze-dried extract as described in Example 1 was intimately mixed with 10 g of fibrous cellulose. Sigma cellulose #6663 is a suitable grade. 70 ml of a mixture of butanol; Industrial Methylated Spirit; water (BIW) in the proportions 4:1:1 was added to the cellulose mixture and stirred for 10 minutes. The mixture was centrifuged (5 minutes at 6,000 rpm). The precipitate was re-suspended with 30 ml BIW and recentrifuged. This operation was repeated and the precipitate dried in a vacuum oven at 60-70° C.

The dried cellulose mixture was then re-suspended in distilled water, stirred for 10 minutes and centrifuged. The precipitate was then washed with 3 further quantities of water and centrifuged, pooling the supernatants. The combined supernatants were evaporated to dryness to give approximately 20 mg of a own solid.

This material when formulated with excipients, filled into capsules, compressed into tablets or dissolved in a pharmaceutically acceptable vehicle is suitable for the treatment of patients with severe atopic eczema. The above example provides a method for producing pharmaceutical preparations of the active components of PSE222 on a commercial scale.

The invention claimed is:

1. A composition for the treatment of a disease selected from the group consisting of atopic disease, non-atopic eczema and psoriasis, which comprises a decoction or extract obtained from the following set of herbs:
   Radix Rehmannia
   Radix Glycyrrhiza
   Radix Paeonia Rubra
   in the substantial absence of any other herb;
   said decoction or extract comprising fractions which run with Rf, values in one or more of the ranges:
   0.00 to 0.100;
   0.167 to 0.300;
   0.400 to 0.533;
   0.700 to 0.833; or
   0.900 to 0.967
   if an aqueous solution of a freeze-dried decoction of said set of herbs is subjected to chromatography on a Whatman 2 cm×55 cm 3 MM cellulose strip for 10 hours using a solvent mixture of butanol, ethanol and water in the proportions 4:1:1.

2. A composition as claimed in claim 1, wherein the decoction or extract comprises one or more fractions which run with Rf values in the range 0.00 to 0.100 under the said chromatography.

3. A composition as claimed in claim 1, wherein the decoction or extract comprises one or more fractions which run with Rf values in the ranges 0.00 to 0.100, 0.167 to 0.300, 0.400 to 0.533, 0.700 to 0.833 or 0.900 to 0.967 which is/are capable of being extracted with water from said chromatography strip.

4. A composition as claimed in claim 1, wherein the decoction or extract comprises one or more of those components running with Rf values in the ranges 0.700 to 0.833 or 0.900 to 0.967 which is capable of being extracted with methanol from said chromatography strip.

5. A composition as claimed in claim 1, wherein the decoction or extract is prepared by a process that includes removing components therefrom which are extractable with hexane or other non-polar solvent.

6. A composition as claimed in claim 1, wherein the decoction or extract is prepared by a process that includes an initial water extraction.

7. A composition as claimed in claim 1, whereby such composition is suitable for the treatment of atopic or non-atopic eczema.

8. A composition as claimed in claim 1, wherein said decoction or extract is present in an amount which causes a percentage inhibition of interleukin 4 (IL4) induced CD23 expression of at least 25% in peripheral blood monocytes.

9. A pharmaceutical composition for the treatment of a disease selected from the group consisting of atopic disease, non-atopic eczema and psoriasis comprising a treatment-effective amount of the composition of claim 1 and a pharmaceutically acceptable carrier or diluent.

10. A pharmaceutical composition as claimed in claim 9, which is formulated for oral, parenteral or topical administration.

* * * * *